United States Patent [19]

Peters

[11] Patent Number: 4,964,417
[45] Date of Patent: Oct. 23, 1990

[54] WOUND CLOSURE DEVICE

[75] Inventor: Joseph L. Peters, Crouch Hill, England

[73] Assignees: Clini-Med Ltd., Graves End; Clinical Product Development Ltd., Bucks, both of England

[21] Appl. No.: 324,430

[22] Filed: Mar. 16, 1989

Related U.S. Application Data

[63] Continuation of Ser. No. 52,854, filed as PCT GB86/00503 on Aug. 22, 1986 published as WO87/01027 on Feb. 26, 1987, abandoned.

[30] Foreign Application Priority Data

Aug. 22, 1985 [GB] United Kingdom ............... 8520999

[51] Int. Cl.⁵ .............................................. A61B 17/00
[52] U.S. Cl. ..................... 128/850; 128/887; 128/888; 606/148
[58] Field of Search ............... 128/303 R, 334 R, 850, 128/887, 888, 851; 446/387, 153, 901; 606/233, 148

[56] References Cited

U.S. PATENT DOCUMENTS

| | | | |
|---|---|---|---|
| 1,275,520 | 8/1918 | Bell | 128/303 R |
| 1,471,885 | 10/1923 | Dessau | 446/153 |
| 2,760,302 | 8/1956 | Cheskin | 446/387 |
| 3,863,639 | 2/1975 | Kleaveland | 128/303 R |
| 4,205,680 | 6/1980 | Marshall | 604/362 |

FOREIGN PATENT DOCUMENTS 837919 5/1952 Fed. Rep. of Germany ... 128/303 R

OTHER PUBLICATIONS

V. Mueller and Co. Guide to Purchasing, 1956, p. 829.

Primary Examiner—Michael H. Thaler
Attorney, Agent, or Firm—Mason, Fenwick & Lawrence

[57] ABSTRACT

A device for assisting wound closure in a surgical procedure in the form of a silicon rubber suture mat (1,3) and having a front region (2) of generally lenticular shape and an integral narrower tail region (3), the sides (3') of which are mutually biconcave with respect to the biconvex sides (2') of the front region (2) and are continuously curved therewith. When closing a wound, the front region (2) is used to cover, protect and retain the internal organs by being tucked under adjacent tissue, with the tail region (3) protruding from the wound. After the wound has been almost completely closed, the mat, due to its shape and inherent flexibility may be smoothly removed through a small remaining wound aperture (11) prior to final closure.

1 Claim, 1 Drawing Sheet

WOUND CLOSURE DEVICE

This application is a continuation of application Ser. No. 052,854 filed as PCT GB86/00503 on Aug. 22, 1986, published as WO87/01027 on Feb. 26, 1987 now abandoned.

FIELD OF THE INVENTION

The present invention relates to a device for assisting wound closure particularly that of a major body cavity which has been opened to permit a surgical procedure to be carried out.

BACKGROUND OF THE INVENTION

During surgical procedures in which a major body cavity has been opened e.g. the abdomen, chest or the pericadial cavity surrounding the heart, it is a fundamental requirement that the wound through the various muscular and membranous layers should be closed at the end of the procedure. This involves restoring the organs and intestine to their normal anatomical situation and approximating together the tissues of the abdomen or chest with various types of surgical needles and suture materials.

Often, in emergency situations, there may be an inadequate number of personal to assist the surgeon who is performing the operation, and furthermore, the intestine and other organs may prolapse out of the relevant cavity to create troublesome technical difficulties for the surgeon and danger to the patient. There is also a continuous risk of injuring the bowel and another structures with a constantly moving needle point in such circumstances. Whilst a variety of rigid metal retractors and spatulas are currently available to help in these circumstances, they require to be held by an assistant and removed early in the wound closure procedure.

SUMMARY OF THE INVENTION

It is an object of the invention to overcome the above difficulties.

According to the invention there is provided a device for assisting wound closure in a surgical procedure, comprising a body of flexible sheet material shaped and configured to be inserted under adjacent tissue during wound closure to cover and retain internal organs exposed by the wound, and providing means for enabling the same to be pulled free through a remaining wound aperture after the wound has been substantially closed.

The above device is capable of acting both as a "third hand" or an assisting surgical tool to retain body organs within their natural cavities and simultaneously serve as a mechanism or barrier to protect the underlying bowel or organs from accidental injury from needles or other surgical instruments during the closure of the wound.

Advantageously the main body portion of the device has a biconvex lenticular or oval shaping which conforms to that of the gaping defect always produced by a surgical wound due to the natural elasticity of the surrounding tissue.

Thus, when of appropriate size, the main body portion can readily be tucked under surrounding tissue prior to wound closure to retain and protect the organs because of its general conformity to the wound opening.

The combined effect of this shaping, with the inherent flexibility of the base material employed, leads to the advantageous result that the main body portion may be readily removed after substantial wound closure since it offers little resistance to the confining and restraining influences of the restricted wound aperture through which it is extracted but readily yields to these forces, without causing damage to the partially closed wound.

BRIEF DESCRIPTION OF THE DRAWINGS

Other features and advantages of the present invention will become apparent from the following specific description of a preferred form of the invention taken with reference to the accompanying drawings wherein.

BEST MODES OF CARRYING OUT THE INVENTION

Figure 1:
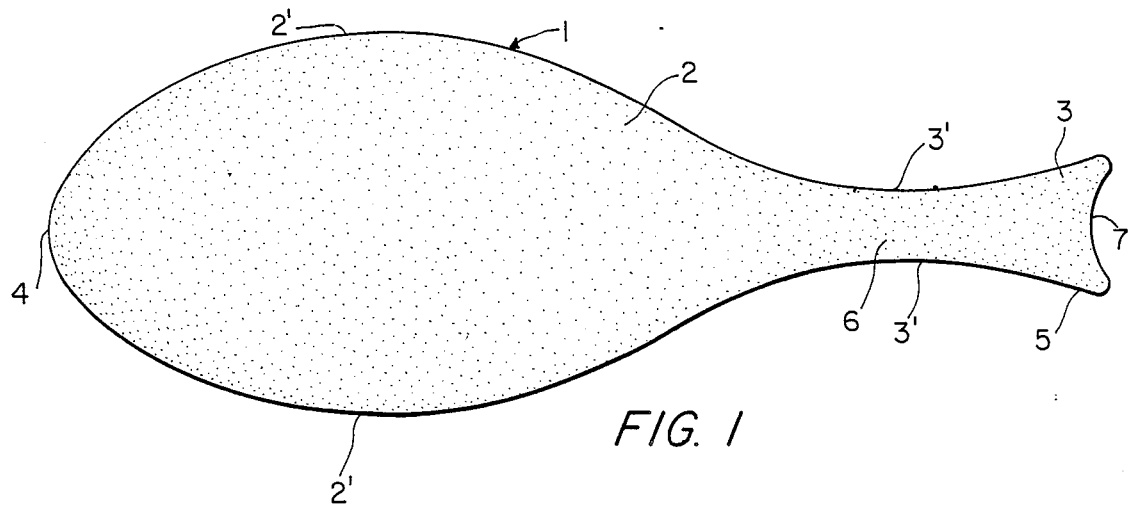
FIG. 1 is a top (or underside) view of a wound closure device according to the invention.

The device for assisting closure of a surgical wound, or suture mat, shown in the drawings, comprises a flat flexible membrane or sheet 1 of silicon rubber or synthetic plastics possessing similar characteristics, which include being radio-opaque to x-rays to allow detection in case of accidental loss within a body capacity. The representative thickness of the membrane or sheet 1 is 2 mm.

The membrane 1 has a broad oblong front region 2 and a narrower rear oblong tail region 3 in axial alignment with and extending longitudinally of the front region 2.

The front region 2 is lenticular or oval in shape defining biconvex sides 2' closing at one end of the region 2 to form a round tip 4, and smoothly reversing curvature at the other end of region 2 to form biconcave sides 3' of the tail region 3.

The concave curving sides 3' terminate to form an end tail portion 5 wider than the narower mid-portion 6 defined by the sides 3'.

The end 7 of the tail region is inwardly curved to match the tip 4.

Figure 2:
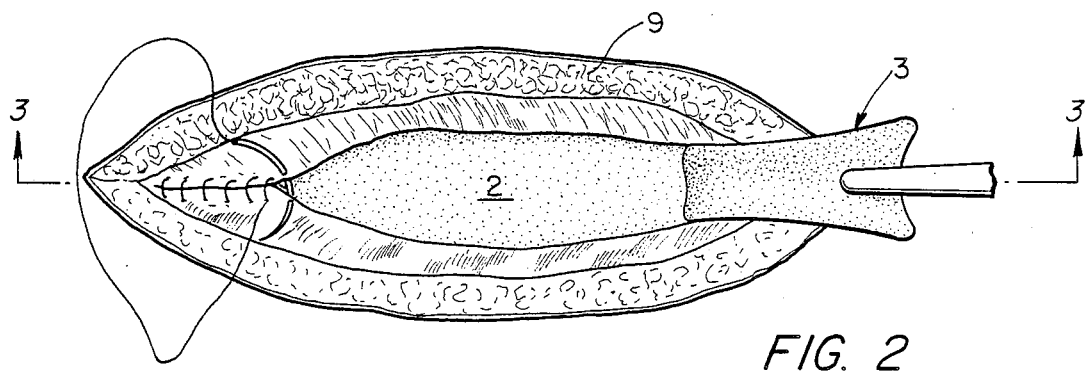
FIG. 2 is a view of the device of FIG. 1 positioned in a stomach wound as the wound is being stitched together.
Figure 3:
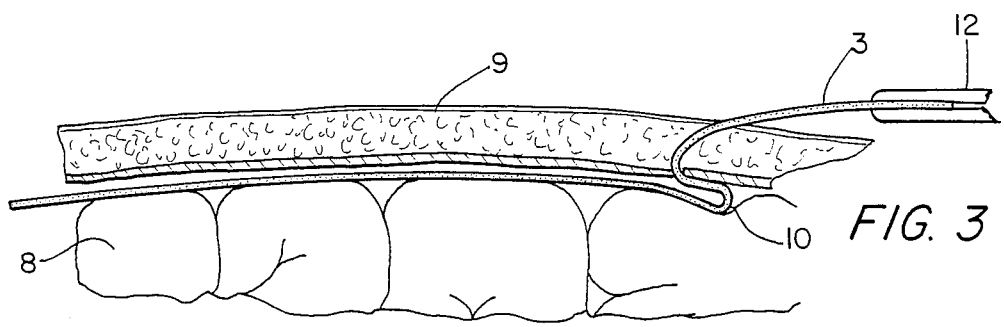
FIG. 3 is a sectional view along the line A—A of FIG. 2.

It may be seen from FIGS. 2 and 3, which picture the use of the device in abdominal surgery, that the device as above described may be slipped between the underlying organs 8 and the abdominal wall 9 with the tail region 3 protruding from the wound and the front region 2 covering and protecting the organs 8.

To enable the organs to be completely covered where the tail region 3 exits from the wound, the tail 3 overlaps the front region 2 at 10 so that the sheet material of the front region 2 may be tucked under the surrounding tissue at this exit point, while due to the narrowing of the tail portion 3 at 6, any widening of the body cavity by the tail portion 3 is avoided.

Figure 4:
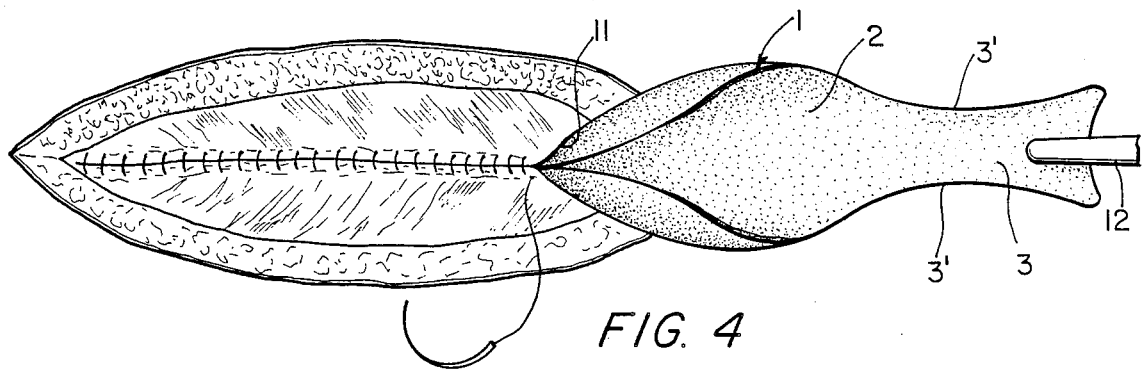
FIG. 4 is a view similar to FIG. 2 showing the device being extracted through a remaining wound aperture after substantial closure of the wound.

After the wound has been almost completely closed over, see FIG. 4, to leave a remaining wound aperture 11, with the front region 2 still protecting the organs 8, the tail region 3 is used to pull the front region 2 of the device through the aperture 11 by means of forceps 12.

As illustrated in FIG. 4, the front region 2 offers no resistance to the constraining effects imposed by the aperture 11, because, due to its inherent flexibility and smoothly curved sides, it simply contracts or folds together to the size of the aperture and slides smoothly through it, to assume its normally expanded state after complete extraction.

Additionally the shape of the device facilitates the manufacturing process by minimising wastage of material when the device is stamped or moulded from rolls of material.

The device may be used in surgical procedures other than abdominal.

Thus it may be employed in the more superficial, e.g., subcutaneous planes of the body to retain and protect delicate artifical prostheses during their surgical insertion.

By way of example, small variants may be used to cover and protect the surface silicon gel breast implants from accidental puncture by suture needles whilst the prostheses are being carefully placed in the correct position.

With the surface of the delicate prostheses covered by the invention, a series of interrupted sutures may be inserted into the appropriate tissues external or superficial to the mat. Finally these may be tightened as the suture mat is simultaneously removed from the operation wound.

I claim:

1. A suture mat for temporary placement in a body to retain and protect body organs during surgical procedures and capable of being withdrawn from the body through a restricted opening therein, said mat comprising a sheet of flexible material comprising:

means for retaining a body organ against displacement and for removal from said body through an opening, said means being a thin body of oblong shape having bi-convex lenticular sides and having substantial lateral and longitudinal extent with the lateral extent greater than the opening, said means being uninflatable and of substantially uniform thickness, and elongate means integral with said oblong retaining means extending from and longitudinally of said oblong retaining means for extraction of said retaining means from a body, said elongate extraction means having a lesser lateral extent than said oblong retaining means and a length greater than the lateral extent thereof and having sides are bi-concave with respect to said bi-convex sides, each bi-convex side of said retaining means continuously curving into a respective concave side of said extraction means, said extraction means having an end thereof remote from said retaining means, said retaining means having a rounded end portion opposite said extraction means, the end of said extraction means having a bi-concave curvature which substantially matches the rounded end portion of said retaining means, said suture mat being without a center reinforcing piece and without means for causing said sheet to be in a substantially vertical plane when immersed in water.

* * * * *